United States Patent
Forsell

(10) Patent No.: US 6,460,543 B1
(45) Date of Patent: Oct. 8, 2002

(54) NON-INJECTION PORT FOOD INTAKE RESTRICTION DEVICE

(75) Inventor: Peter Forsell, Alvsjo (SE)

(73) Assignee: Obtech Medical AG, Baar (CH)

( * ) Notice: Subject to any disclaimer, the term of this patent is extended or adjusted under 35 U.S.C. 154(b) by 0 days.

(21) Appl. No.: 09/133,322

(22) Filed: Aug. 13, 1998

(51) Int. Cl.[7] .............................................. A61B 19/00
(52) U.S. Cl. ........................ 128/898; 606/151; 606/157; 606/192
(58) Field of Search .................... 128/897–98; 600/593, 600/31; 606/151, 157, 191, 192, 195, 213, 228; 604/28, 51, 97, 99

(56) References Cited

U.S. PATENT DOCUMENTS

| 4,592,339 A | 6/1986 | Kuzmak et al. |
| 4,592,355 A | 6/1986 | Antebi |
| 4,696,288 A | 9/1987 | Kuzmak et al. |
| 5,074,868 A | 12/1991 | Kuzmak |
| 5,226,429 A | 7/1993 | Kuzmak |
| 5,771,903 A | 6/1998 | Jakobsson |

FOREIGN PATENT DOCUMENTS

| EP | 611 561 | 8/1994 |
| WO | WO 94/27504 | 12/1994 |

Primary Examiner—John P. Lacyk
(74) Attorney, Agent, or Firm—Nixon & Vanderhye P.C.

(57) ABSTRACT

A food intake restriction device for forming a stoma opening in the stomach or esophagus of a patient, comprises an elongated restriction member forming an expandable and contractible cavity formed into an at least substantially closed loop defining a restriction opening, the size of which is reduced upon expansion of the cavity and increased upon contraction of said cavity. A reservoir containing a predetermined amount of hydraulic fluid and connected to the cavity of the restriction member, and a hydraulic operation device for distributing fluid from the reservoir to the cavity to expand the cavity and for distributing fluid from the cavity to the reservoir to contract the cavity, are also implanted in a patient with morbid obesity and operated from outside the patient's body in a non-invasive manner. A non-inflatable restriction member may alternatively be use, and hydraulically adjusted.

112 Claims, 6 Drawing Sheets

NO FLOW

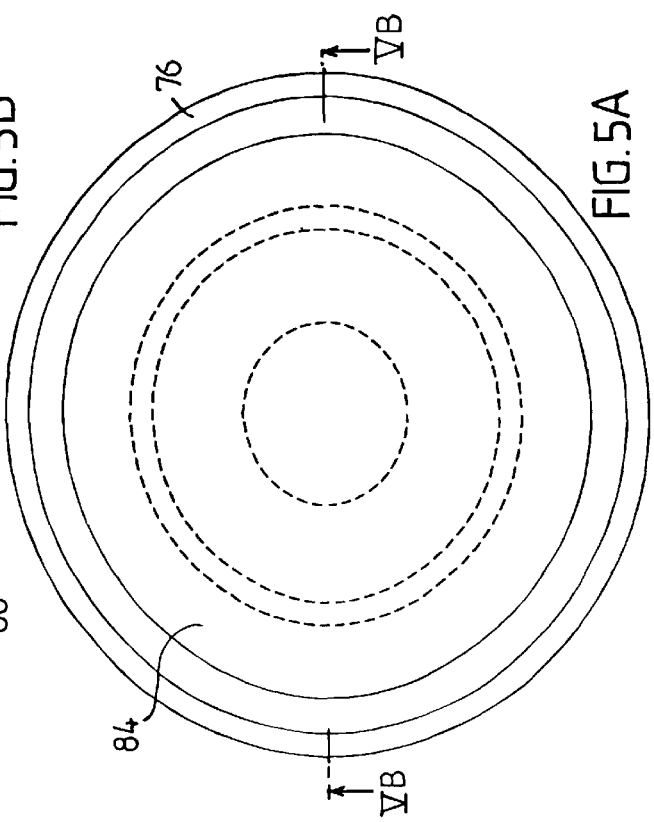
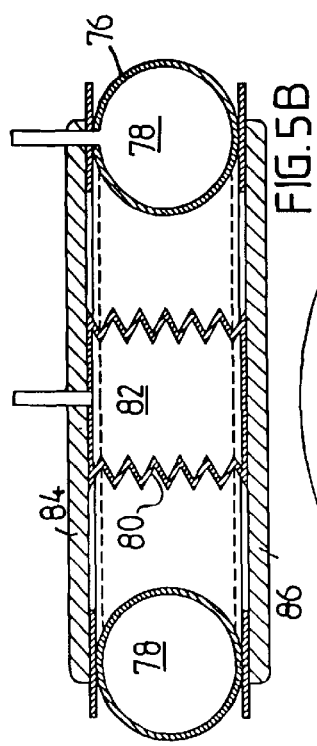
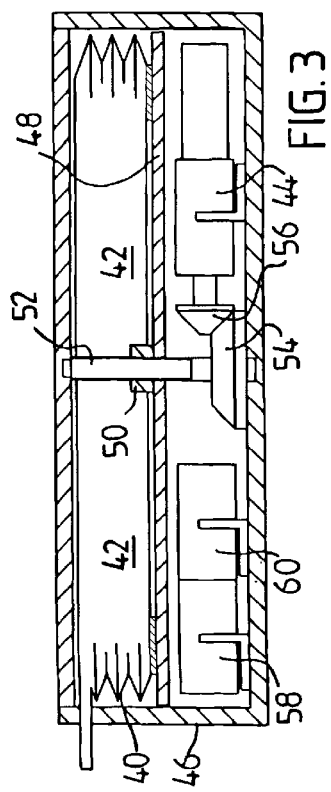
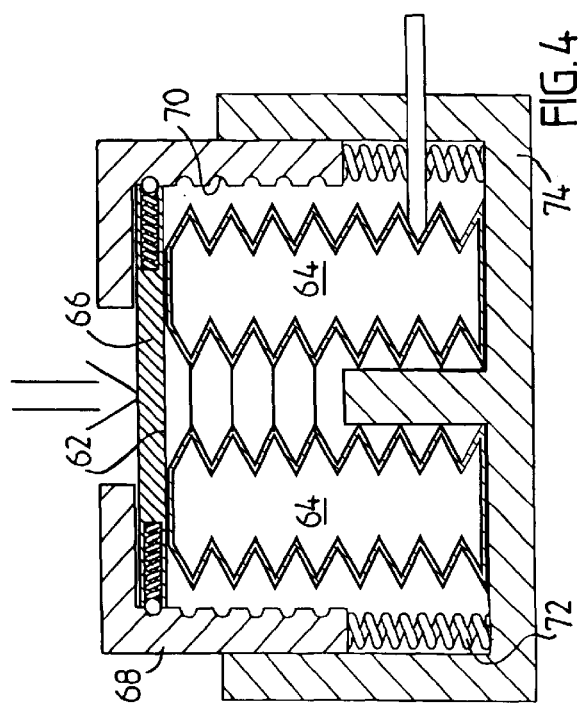

NON-INJECTION PORT FOOD INTAKE RESTRICTION DEVICE

BACKGROUND AND SUMMARY OF THE INVENTION

The present invention relates to a food intake restriction device for the treatment of morbid obesity. More specifically, the invention relates to a food intake restriction device for surgical application in the abdomen of a patient for forming a stoma opening in the stomach or esophagus of the patient.

Food intake restriction devices in the form of gastric banding devices, in which an elongated restriction member in the form of a band encircles a portion of the stomach, have been used in surgery for morbid obesity to form a small gastric pouch above the band and a reduced stoma opening in the stomach. Although such a band is applied around the stomach to obtain an optimal stoma opening during surgery, some prior gastric banding devices are provided with a control means enabling minor post-operation control of the size of the stoma opening. The control means in such prior art devices as disclosed, for example, in U.S. Pat. No. 4,592,339, European Patent No. 0611561 and International Patent Application WO 94/27504, comprise an inflatable cavity in the band and an injection port in fluid connection with the inflatable cavity for adding fluid to or withdrawing fluid from the lafter. In practice, the band is made of silicone rubber which is a material approved for implantation and the fluid is a liquid such as an isotonic salt solution.

It has been found, however, that the prior bands later might dislocate downwardly on the stomach and there is an increased risk of stoma stenosis due to too limited control of the band. It has also been found that the volume of the gastric pouch above the band increases in size up to ten times after the operation. Therefore the pouch volume during surgery needs to be very small, approximately 7 ml. To enable the patient to feed the stomach with sufficient nutrition immediately after the operation considering such a small gastric pouch, the stoma initially needs to be relatively large and later needs to be substantially reduced, as the pouch volume increases. To be able to achieve acceptable control of the band, the cavity in the band has to be relatively large and be defined by a thin flexible wall, normally made of silicone material. Furthermore, the size of the stoma opening has to be gradually reduced during the first year after surgery as the gastric pouch increases in size. As indicated above, the reduction of the stoma opening by using the prior art gastric banding devices is achieved by adding liquid to the cavity of the band via the injection port to expand the band radially inwardly.

A great disadvantage of repeatedly injecting liquid via the injection port is the increased risk of the patient getting an infection in the area surrounding the injection port. If such an infection occurs the injection port has to be surgically removed from the patient. Moreover, such an infection might be spread along the tube interconnecting the injection port and the band to the stomach causing even more serious complications. Thus, the stomach might be infected where it is in contact with the band, which might result in the band migrating through the wall of the stomach. Also it is uncomfortable for the patient when the necessary, often many, post-operation controls of the stoma opening are carried out by using an injection needle penetrating the skin of the patient into the injection port.

Also the patient may swallow pieces of food that are too large and therefore cannot pass the restricted stoma opening. In this case the patient has to visit a doctor who can remove the food pieces, if the band design so permits, by withdrawing some liquid from the band to enlarge the stoma opening to allow the food pieces to pass the stoma. Then, the doctor has to add liquid to the band in order to regain the restricted stoma opening. Again, these measures require the use of an injection needle penetrating the skin of the patient, which is uncomfortable for the patient.

Another problem with the known adjustable gastric banding devices is that there is a risk of leakage from the band balloon occurring some time after the operation.

The invention provides an adjustable food intake restriction device which does not require the use of an injection needle for accomplishing post-operation adjustments of the stoma opening. Rather, the invention provides an adjustable food intake restriction device which permits post-operation adjustments that are comfortable for the patient, and which reduces the risk of liquid leaking from the device.

In accordance with a broad aspect of the present invention, a food intake restriction device is provided for surgical application in the abdomen of a patient for forming a stoma opening in the stomach or esophagus of the patient, the device comprising: an elongated non-inflatable restriction member formed into at least a substantially closed loop around the stomach or the esophagus, the loop defining a restriction opening, an adjustment device which mechanically adjusts the restriction member in the loop to change the size of the restriction opening, hydraulic operation means for operating the adjustment device, and a reservoir containing a predetermined amount of hydraulic fluid for supplying the hydraulic operation means with hydraulic fluid.

In accordance with a specific aspect of the present invention, a food intake restriction device is provided for forming a stoma opening in the stomach or esophagus of a patient, comprising: an elongated restriction member forming an expandable and contractible cavity formed into an at least substantially closed loop around the stomach or esophagus of the patient and defining a restriction opening, the size of which is reduced upon expansion of the cavity and increased upon contraction of the cavity, a reservoir containing a predetermined amount of hydraulic fluid and connected to the cavity of the restriction member, and a hydraulic operation means for distributing fluid from the reservoir to the cavity to expand the cavity and for distributing fluid from the cavity to the reservoir to contract the cavity.

Thus, there is no need for an injection port for accomplishing necessary post-operation adjustments of the restriction opening to change the size of the stoma opening. (In certain applications, however, an injection port connected to the reservoir may be provided for enabling, normally a single once-and-for-all, calibration of the predetermined amount of fluid in the reservoir.)

In accordance with a general embodiment of the invention, the reservoir defines a chamber for the predetermined amount of fluid and the hydraulic operation means changes the size of the chamber. Preferably, the hydraulic operation means comprises first and second wall portions of the reservoir, which are displaceable relative to each other to change the size of the chamber of the reservoir. The hydraulic operation means may distribute fluid from the reservoir to the cavity of the restriction member in response to a predetermined first displacement of the first wall portion of the reservoir relative to the second wall portion of the reservoir and to distribute fluid from the cavity to the reservoir in response to a predetermined second displacement of the first wall portion relative to the second wall portion.

The first and second wall portions of the reservoir may be displaceable relative to each other by manual manipulation thereof, such as by manually pushing, pulling or rotating any of the wall portions in one direction, or alternatively, may be displaceable relative to each other by a device powered magnetically, hydraulically, or electrically (e.g. by an electric motor). In this embodiment no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

In accordance with a particular embodiment of the invention, the hydraulic operation means comprises an activatable pump for pumping fluid between the reservoir and the cavity of the restriction member. The pump preferably comprises a first activation member for activating the pump to pump fluid from the reservoir to the cavity of the restriction member, and a second activation member for activating the pump to pump fluid from the cavity to the reservoir. The first and second activation members may be operable by manual manipulation thereof, such as by manually pushing, pulling or rotating any of the activation members in one direction. At least one of the activation members is constructed to operate when subjected to an external pressure exceeding a predetermined magnitude.

As an alternative to the manual manipulation, at least one of the first and second activating members may be operable by a device powered magnetically, hydraulically, or electrically (e.g. by an electric motor). The pump may pump fluid both to and away from the adjustment device or hydraulic means controlling the adjustment device. A mechanical manual solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated either manually, mechanically, electrically, magnetically, or hydraulically. Any kind of motor could be used for the different operations s well as wireless remote solutions.

Wherever a magnetic means is utilized according to the invention it may comprise a permanent magnet and a magnetic material reed switch, or other suitable known or conventional magnetic devices.

In accordance with another particular embodiment of the invention, the hydraulic operation means comprises a servo means, suitably including a hydraulic device. Alternatively, the servo means may include magnetic or electric means. Preferably, the servo means comprises a servo reservoir defining a chamber containing servo fluid and the hydraulic operation means comprises first and second wall portions of the servo reservoir, which are displaceable relative to each other to change the size of the chamber of the servo reservoir. The same principle will apply for the servo reservoir as for the earlier described reservoir wherein the volume in the servo reservoir may be increased or decreased by a first or second displacement of the first wall portion relative to the second wall portion of the servo reservoir and thereby control the earlier described reservoir and thereby indirectly control the restriction opening. The first and second wall portions of the servo reservoir may be displaceable relative to each other by manual manipulation thereof, such as by manually pushing, pulling or rotating any of the wall portions of the servo reservoir in one direction. Alternatively, the first and second wall portions may be displaceable by magnetically, hydraulically or electrically powered devices. These powered devices may all be activated by manual manipulating means preferably located subcutaneously. This activation may be indirect, for example via a switch.

Advantageously, especially when manual manipulation means are used, a servo means system could be used. With servo means less force is needed for controlling the adjustment device. Hydraulic operation is preferably used with servo means. One example is a closed system that controls another closed system in which the hydraulic means of the adjustment device is incorporated. Minor changes in the amount of fluid in a reservoir of the first system could then lead to major changes in the amount of fluid in a reservoir in the second system. Consequently, the change in volume in the reservoir of the second system affects the hydraulic operation of the adjustment device which is incorporated in the second closed system. The great advantage of this servo system is that the larger volume system could be placed inside the abdomen where there is more space and still it would be possible to use manual manipulation means of the smaller system subcutaneously. The servo reservoir could control the reservoir of the larger volume. The servo reservoir could be controlled directly or indirectly by a fluid supply means. The fluid supply means may be a small reservoir, which may be placed subcutaneously and may be activated by manual manipulation means controlling the servo reservoir, or other suitable device.

Preferably, the fluid supply means comprises hydraulic means and a fluid supply reservoir defining a chamber containing fluid, and the hydraulic operation means comprises first and second wall portions of the reservoir, which are displaceable relative to each other to change the size of the chamber of the fluid supply reservoir. The hydraulic operation means may distribute fluid from the fluid supply reservoir to the servo reservoir in response to a predetermined first displacement of the first wall portion of the fluid supply reservoir relative to the second wall portion of the fluid supply reservoir and to distribute fluid from the servo reservoir to the fluid supply reservoir in response to a predetermined second displacement of the first wall portion relative to the second wall portion. The wall portions of the fluid supply reservoir may be displaceable relative to each other by manual manipulation means or be displaceable relative to each other by manual manipulating means for pushing, pulling or rotating any of the wall portions of the fluid supply reservoir in one direction. Alternatively, the wall portions of the fluid supply reservoir may be displaceable relative to each other by magnetic means, hydraulic means, manually manipulated means, or electrical control means including an electric motor. The magnetic means, hydraulic means, or electrical control means may all be activated by manually manipulated means preferably located subcutaneously. This control may be indirect, for example via a switch.

Even in the broadest embodiment of the invention the adjustment device may comprise a servo means. The servo means may comprise a hydraulic operation means, an electric control means, a magnetic means, mechanical means, or a manual manipulating means. The hydraulic operation means, electric control means, mechanical means or magnetic means may be activated by manual manipulating means. Using a servo system will save the use of force when adjusting the adjustment device which may be of importance in many applications.

All systems according to the invention may be controlled by a wireless remote control means.

In accordance with an advantageous embodiment of the invention, there is provided a wireless remote control means for controlling the hydraulic operation means and comprising a separate signal transmitting means and a signal receiving means for controlling the hydraulic operation means in response to signals received from the signal transmitting means. Preferably, the remote control means comprises a motor for operating the hydraulic operation means and an energizer unit for providing energy, and the signal receiving means comprises a control unit powering the motor with energy provided by the energizer unit in response to signals received from the signal transmitting means. In this case the energizer unit may be a battery. The wireless remote control may control the adjustment device and any type of hydraulic operation means including servo means and fluid supply means. The remote control also could control any of the other described embodiments including any kind of servo means. Advantageously, the signal transmitting means also transmits electromagnetic wave signals and the energizer unit draws radiant energy from the electromagnetic wave signals as they are transmitted to the signal receiving means and transfers the radiant energy into electric energy for powering the electric motor.

To expand the field of application, the energizer unit may comprise a rechargeable electric power supply, such as a capacitor, for storing the electric energy and the control unit may power the electric motor, for instance a stepping motor, with energy from the rechargeable electric power supply in response to signals received from the signal transmitting means. In an initial charging step the rechargeable power supply can be charged over a relatively long time (e.g. a few seconds up to a half hour) without powering the electric motor. In a following operating step, when the power supply has been charged with sufficient energy, the control unit powers the electric motor with energy from the charged power supply to operate the adjustment device, so that a desired change of the patient's stoma opening is achieved. If the capacity of the power supply is significant to achieve the necessary adjustment in one single operating step, the above steps may conveniently be repeated until the desired adjustment is achieved.

As an alternative, the energizer unit may comprise a battery, an electrically operable switch connecting the battery to the signal receiving means in an "on" mode when the switch is powered and to keep the battery disconnected from the signal receiving means in a "standby" mode when the switch is unpowered, and a rechargeable electric power supply for powering the switch. The control unit may power the electric motor with energy from the battery in response to signals received from the signal transmitting means, when the switch is in its "on" mode. Suitably, the energizer unit may transfer the radiant energy into a current for charging the rechargeable electric power supply, such as a capacitor.

The energizer unit may comprise a coil connected to the signal receiving means for inducing an alternating current as electromagnetic wave signals are transmitted through the coil to the signal receiving means and a rectifier for rectifying the alternating current.

The non-inflatable embodiment of the restriction member and the adjustment device utilized according to the invention may be as shown in a copending application entitled "Mechanical Food Intake Restriction Device" filed the same date as this application (attorney docket 2333-11), the disclosure of which is hereby incorporated by reference herein.

The invention also relates to a method of treating morbid obesity, comprising: (a) Surgically implanting in the abdomen of a patient with morbid obesity a food intake restriction device which forms a stoma opening in the stomach or esophagus, by forming an elongated restriction member (e.g. of bio-compatible material, or covered with bio-compatible material) into at least a substantially closed loop around the stomach or the esophagus of the patient, the loop defining a restriction opening; and then (b) when necessary for the patient's health or desired progress, in a non-invasive procedure, hydraulically acting on the restriction member to change the size of the restriction opening. Where the restriction member comprises a cavity which can be expanded and contracted by the supply of hydraulic fluid thereto, then (a) may be practiced in part by implanting in the patient a reservoir containing a predetermined amount of hydraulic fluid and connecting the reservoir to the cavity and a hydraulic operation means for distributing fluid from the reservoir to the cavity; and (b) may be practiced by controlling the hydraulic operation means from a point outside the patient's body without physically penetrating the patient's body. Where the restriction member is acted upon by an adjustment device which mechanically adjusts the loop, then (a) may be practiced in part by implanting in the patient the adjustment device, implanting a reservoir containing a predetermined amount of hydraulic fluid and connecting the reservoir to the cavity, and implanting a hydraulic operation means for distributing fluid from the reservoir to the cavity; and (b) may be practiced by controlling the hydraulic operation means from a point outside the patient's body without physically penetrating the patient's body to control the adjustment device so that the size of the restriction opening is changed. This may be done manually, remotely, by remote control, or in the other described manners.

In the method (a) may be practiced by laparoscopic techniques, e.g. by (i) inflating the patient's abdomen with gas by penetration of the patient's skin, (ii) introducing at least two laparoscopic trocars into the abdomen to introduce the elongated restriction member and one or more medical instruments, and then (iii) forming the elongated restriction member into the at least substantially closed loop.

It is the primary object of the present invention to provide an advantageous yet relatively simple assembly and method for treating morbid obesity in a substantially non-invasive manner after initial surgical implantation of a restriction member. This and other objects will become clear from the detailed description and from the appended claims.

BRIEF DESCRIPTION OF THE DRAWINGS

FIG. 3 is a cross-sectional view of a reservoir having a variable volume controlled by a remote control motor, in accordance with a particular embodiment of the principal embodiment shown in FIG. 1B or 2B,.

FIG. 4 is a cross-sectional view of a reservoir having a variable volume adjustable by manual manipulation, in accordance with a particular embodiment of the principal embodiment shown in FIG. 1B or 1D.

FIG. 5A is a perspective view of a hydraulic, pneumatic or mechanical servo system in accordance with a particular embodiment of the principal embodiment shown in FIG. 1D.

FIG. 5B is a cross-sectional view taken along line VB—VB of FIG. 5A.

DETAILED DESCRIPTION OF THE DRAWINGS

Figure 1A:
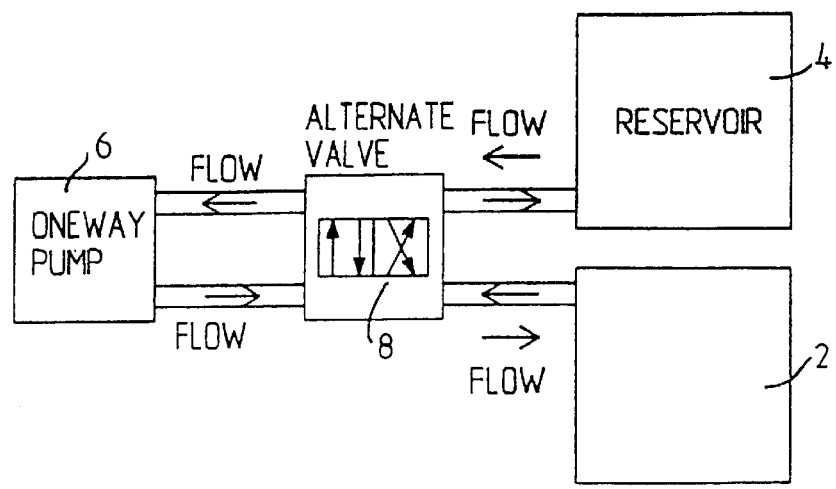
FIGS. 1A–D are block diagrams of four different principal embodiments of the invention.
Figure 1B:
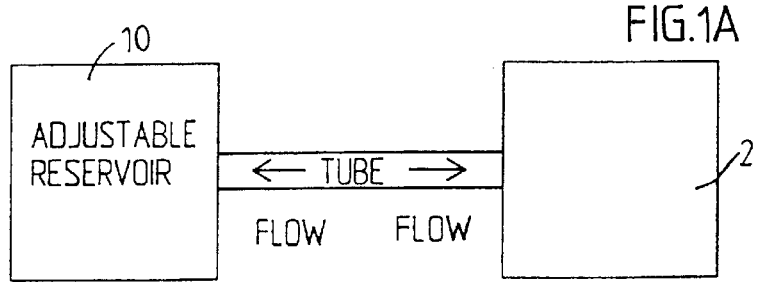
Figure 1C:
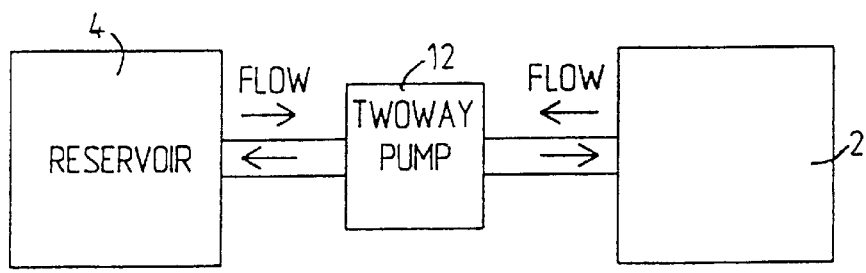
Figure 1D:
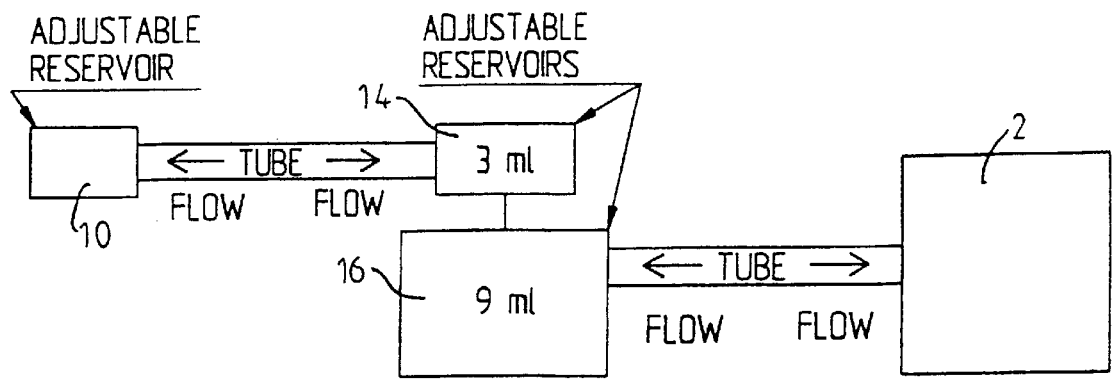
Figure 8:
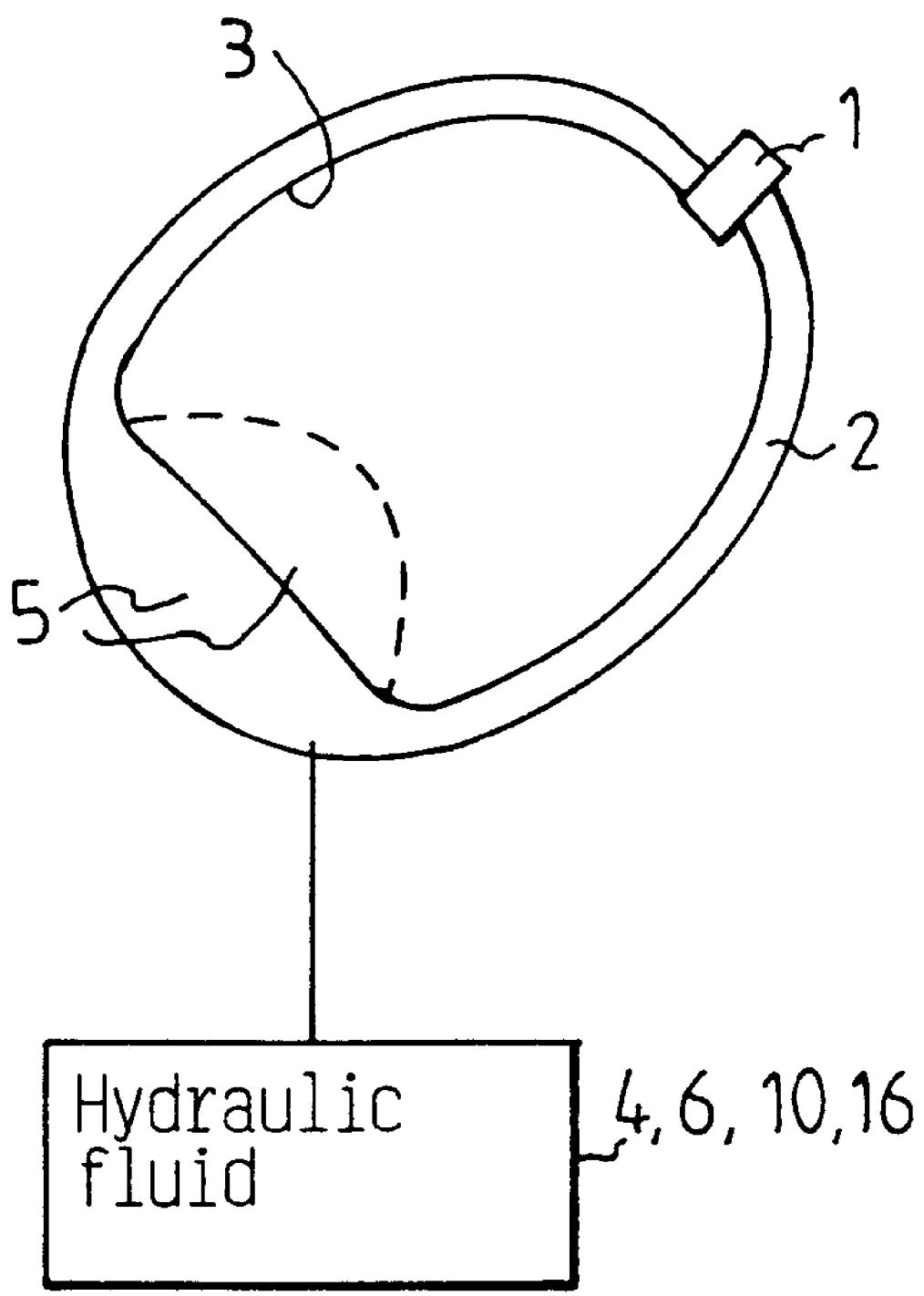
FIG. 8 is a schematic view of a band with a cavity defining a restriction opening for use in accordance with the invention.

FIGS. 1A–D is a block diagram of four different embodiments. FIG. 1A shows a restriction member in the form of a typically conventional inflatable band 2 (SAGB), a separate reservoir 4, a one way pump 6 and an alternate valve 8. FIG. 1B shows the band 2 and a fluid supply reservoir 10. FIG. 1C shows the band 2, a two way pump 12 and the reservoir 4. FIG. 1D shows a servo system with a first closed system controlling a second system. The servo system comprises the fluid supply reservoir 10 and a servo reservoir 14. The servo reservoir 14 controls a larger adjustable reservoir 16 which in connection with the band 2 varies the volume of a cavity in the band, which in turn varies a restriction opening 3 in the band 2. Such a band 2 and opening 3 are illustrated schematically in FIG. 8. The conventional band 2 has an expandable/contractable cavity 5 which is expanded or contracted by supplying hydraulic fluid (e.g. from 4, 6, 10, 16), and the band 2 may be sutured in place, illustrated schematically at 7 in FIG. 8.

Figure 2A:
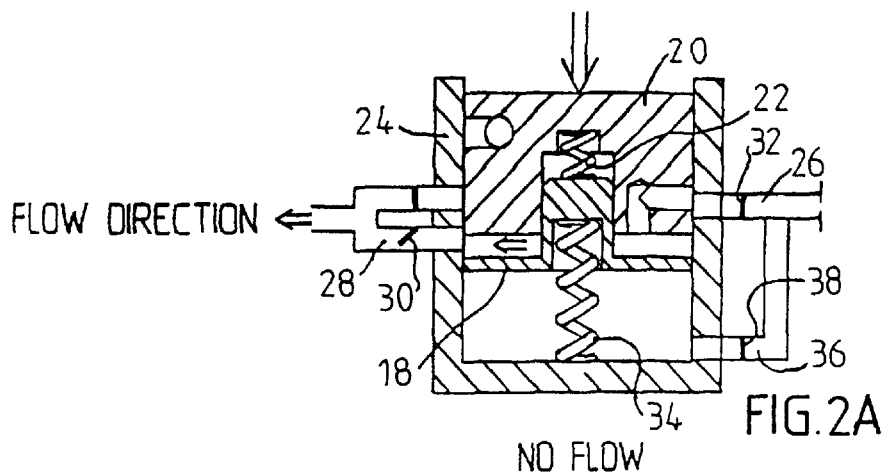
FIGS. 2A–D are cross-sectional views of a pump mechanism according to FIG. 1C, which is designed to pump fluid in opposite directions by mechanically pushing a wall portion in only one direction.
Figure 2B:
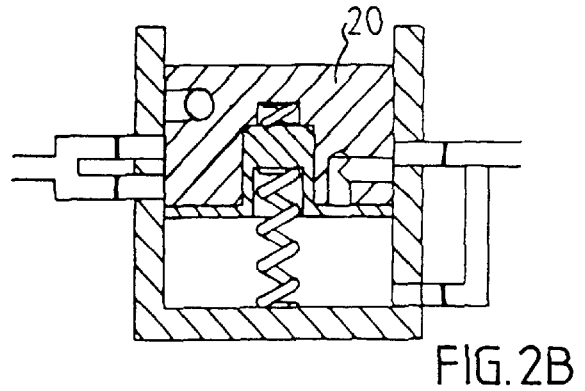
Figure 2C:
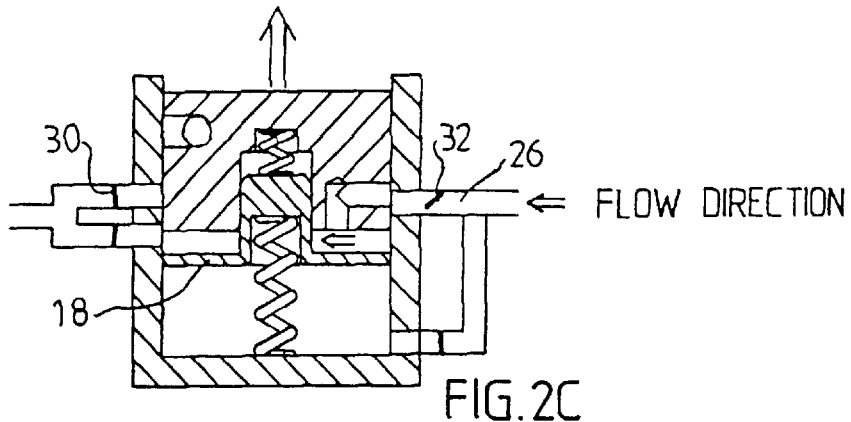
Figure 2D:
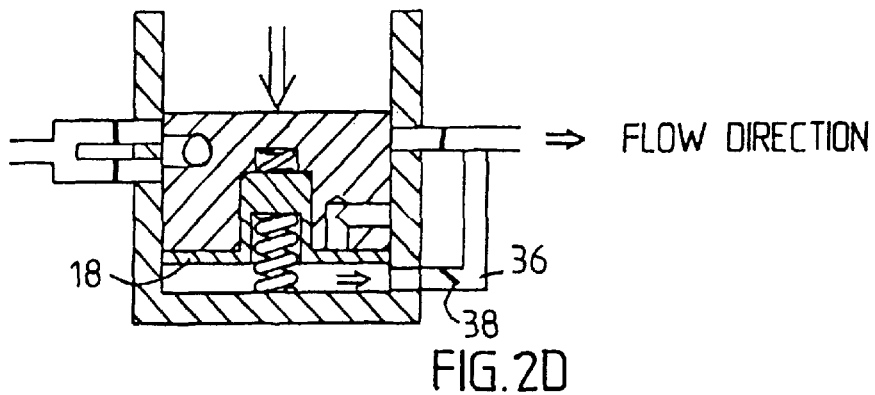

FIGS. 2A–D are cross-sectional views of a pump mechanism for pumping fluid in both directions only by mechanically pushing a separate sealing wall portion 18 in one direction. FIG. 2A shows a piston 20 pushed forwards against a spring 22 towards the wall portion 18 and located in a pump housing 24 conducting fluid from a right upper fluid passage 26 of the housing 24 to a left fluid passage 28 of the housing 24. A main valve 30 is open and a nonreturn valve 32 is closed. FIG. 2B illustrates the first pump movement in which the piston 20 has moved forwards and reaches the wall portion 18. FIG. 2C illustrates how the piston 20 moves backwards by the action of the spring 22. The main valve 30 is now closed and the nonreturn valve 32 is open for fluid from the right upper passage 26. FIG. 1D illustrates how the piston 20 is moved further downwardly from its position according to FIG. 2B while pushing the wall portion 18 downwardly against a second spring 34 that is stronger than spring 22, so that fluid escapes from a right lower fluid passage 36. When moving the piston 20 backwardly from the position according to FIG. 2D, fluid enters the left fluid passage 28 and a valve 38 in the lower right fluid passage 36 closes.

FIG. 3 is a cross-sectional view of a reservoir 40 defining a chamber 42, the size of which is variable and is controlled by a remote controlled electric motor 44, in accordance with FIG. 1B or 1D. The reservoir 40 and the motor 44 are placed in a housing 46. The chamber 42 is varied by moving a large wall 48. The wall 48 is secured to a nut 50, which is threaded on a rotatable spindle 52. The spindle 52 is rotated by the motor 44 via an angular gearing, which comprises two conical gear wheels 54 and 56 in mesh with each other. The motor 44 is powered by a battery 58 placed in the housing 46. A signal receiving means 60 for controlling the motor 44 is also placed in the housing 46. Alternatively, the battery 58 and the signal receiving means 60 may be mounted in a separate place. The motor 44 may also be powered by transmitted electromagnetic wave signals.

FIG. 4 is a cross-sectional view of a reservoir 62 defining a chamber 64, the size of which is variable and is controlled by manual manipulation. A gable wall portion 66 of an open ended inner cylindrical housing 68 is adapted to be pushed downwards to fit in a desired locking groove 70 of a plurality of locking grooves 70 on the mantle wall of the cylindrical housing 68, to reduce the size of the chamber 64. The inner cylindrical housing 68 is suspended by springs 72 and is telescopically applied on an outer cylindrical housing 74. When pushing the inner cylindrical housing 68 it moves downwards relative to the outer cylindrical housing 74 causing the gable wall portion 66 to release from the locking groove 70 and move upwards relative to the inner cylindrical housing 68. When the inner housing 68 is moved upwardly by the action of the springs 72 the size of the chamber 64 is increased.

FIGS. 5A and 5B show a servo means comprising a main ring-shaped fluid reservoir 76 defining a chamber 78, the size of which is variable. Centrally positioned in the main ring-shaped reservoir 76 there is a servo fluid reservoir 80 defining a chamber 82, the size of which is variable. The chamber 82 of the servo reservoir 80 is substantially smaller than the chamber 78 of the main reservoir 76. The two reservoirs 76 and 80 are situated between two opposite separate walls 84 and 86, and are secured thereto. When changing the amount of fluid in the servo reservoir 80, the two opposite walls 84,86 are moved towards or away from each other, whereby the size of the chamber 78 of the main reservoir 76 is changed.

Figure 6:
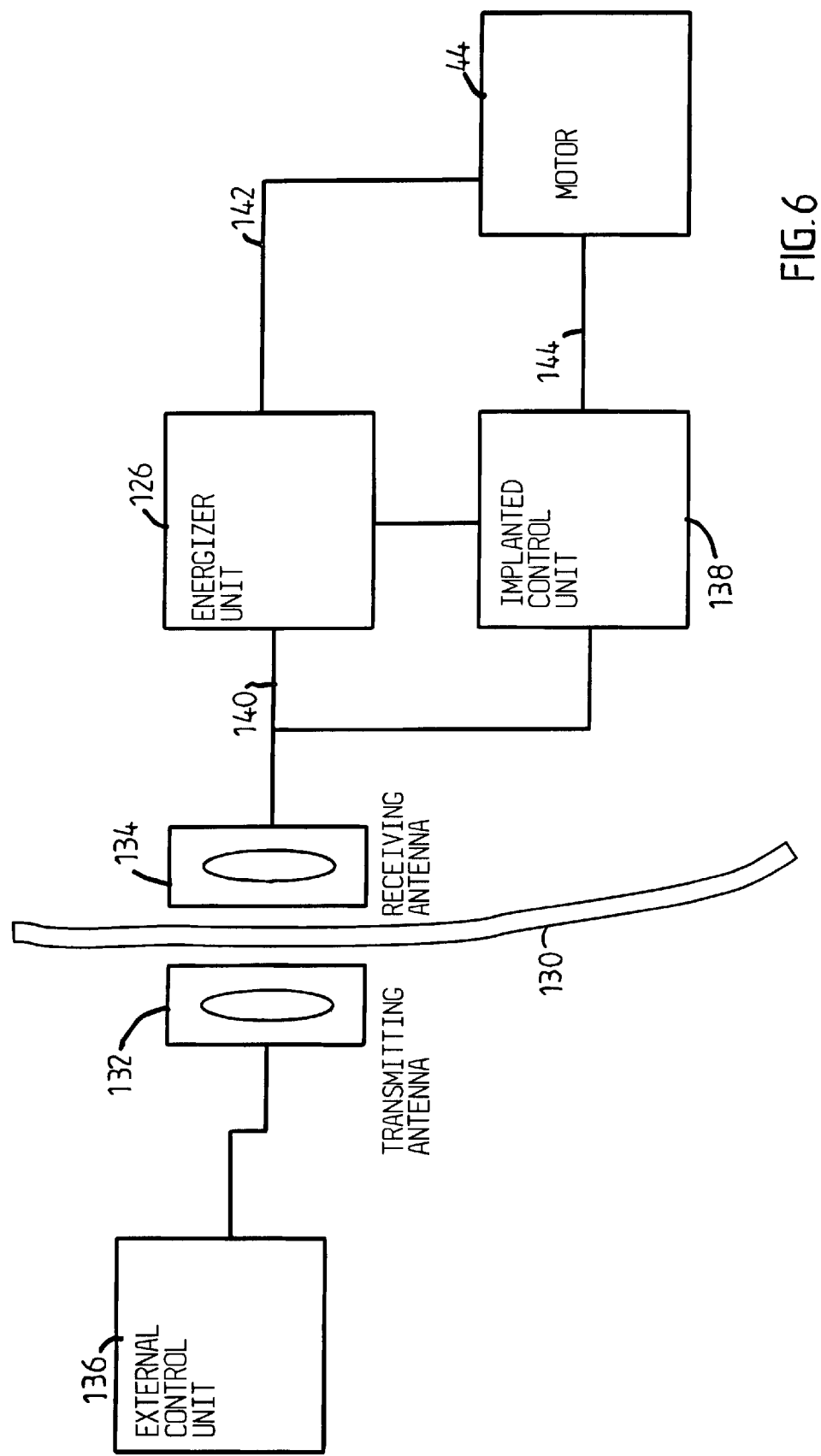
FIG. 6 is a block diagram illustrating remote control components of the device of the invention.

FIG. 6 shows the basic parts of a remote control system of the device of the invention including the electric motor 44 of the embodiment shown in FIG. 3. The described remote control system is also based on the transmission of electromagnetic wave signals, often of high frequencies in the order of 100 kHz–1 gHz, through the skin 130 of the patient. In FIG. 6, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 switches the generator on/off and modulates signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either increase or decrease the size of the restriction opening defined by the loop of the restriction member 2. The microprocessor starts a command by applying a high frequency signal on the antenna 132. After a short time, when the signal has energized the implanted parts of the control system, commands are sent to increase or decrease the size of the restriction opening of the restriction member 2 in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously over a relatively long time period (e.g. about 30 seconds or more). When a new increase or decrease step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 44 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 44 to either increase or decrease the size of the restriction opening of the restriction member 2 depending on the received command code.

Alternatively, the energy stored in the power supply of the energizer unit may only be used for powering a switch, and the energy for powering the motor 44 may be obtained from another implanted power source of relatively high capacity, for example a battery. In this case the switch is adapted to connect the battery to the control unit 138 in an "on" mode when the switch is powered by the power supply and to keep the battery disconnected from the control unit in a standby mode when the switch is unpowered.

Figure 7:
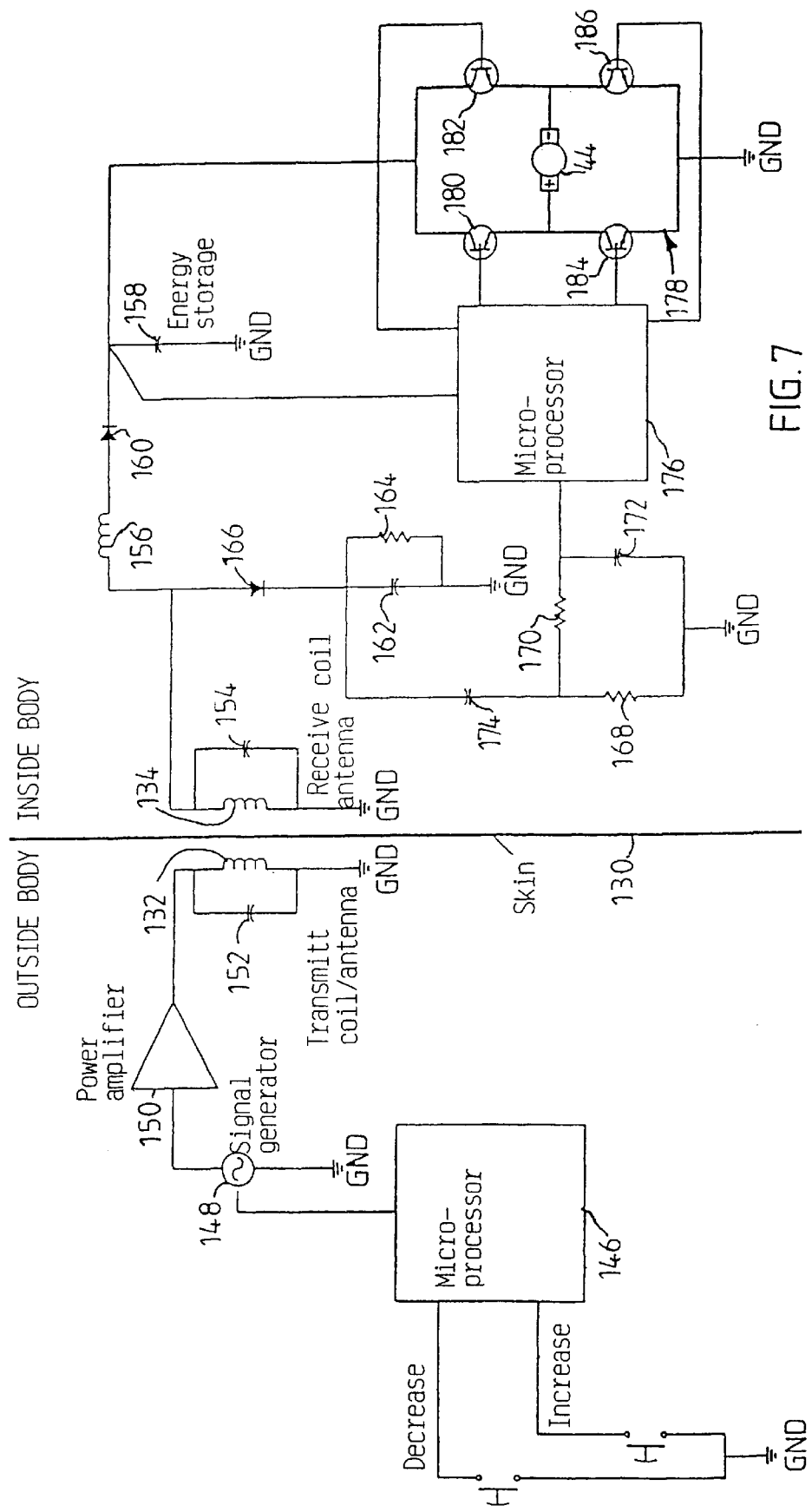
FIG. 7 is a schematic view of exemplary circuitry used for the block diagram of FIG. 6.

With reference to FIG. 7, the remote control system schematically described above will now be described in accordance with a more detailed embodiment. The external control unit 136 comprises a microprocessor 146, a signal generator 148 and a power amplifier 150 connected thereto. The microprocessor 146 switches the signal generator 148 on/off and modulates signals generated by the signal generator 148 with digital commands that are sent to implanted components of the food intake restriction device. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 44 via an H-bridge 178 comprising transistors 180,182,184 and 186. The motor 44 can be driven in two opposite directions by the H-bridge 178.

The microprocessor 176 also monitors the amount of stored energy in the storage capacitor 158. Before sending signals to activate the motor 44, the microprocessor 176 checks whether the energy stored in the storage capacitor 158 is enough. If the stored energy is not enough to perform the requested operation, the microprocessor 176 waits for the received signals to charge the storage capacitor 158 before activating the motor 44.

There are a number of other conceivable alternative embodiments of the invention that give the same result as the above-described embodiments. For example, the microprocessor of the external and implanted, respectively, control units may be replaced by discrete components. The power amplifier of the external control unit may be omitted if the signals generated by the signal generator are strong enough. Therefore the invention is to be accorded the broadest interpretation of the appended claims to encompass all equivalent structures, assemblies, and methods.

What is claimed is:

1. A food intake restriction device for forming a stoma opening in the stomach or esophagus of a patient, comprising:

an elongated restriction member implanted in the patient forming an expandable and contractible cavity, said elongated restriction member formed into an at least substantially closed loop surrounding the patient's stomach or esophagus, and defining a restriction opening, the size of which is reduced upon expansion of said cavity and increased upon contraction of said cavity;

a reservoir implanted in the patient containing a predetermined amount of hydraulic fluid and connected to said cavity of said restriction member, hydraulic operation means implanted in the patient for distributing fluid from said reservoir to said cavity to expand said cavity, and for distributing fluid from said cavity to said reservoir to contract said cavity, to thereby control the size of the restriction opening, and wherein said hydraulic operation means comprises an activatable pump for pumping fluid between said reservoir and said cavity of said restriction member; and wherein said pump comprises a first activation member for activating said pump to pump fluid from said reservoir to said cavity of said restriction member and a second activation member for activating said pump to pump fluid from said cavity to said reservoir; and wherein at least one of said first and second activating members are operable by magnetic means, or by hydraulic means, or by electric control means such as an electric motor.

2. The device according to claim 1, wherein said reservoir defines a chamber for said predetermined amount of fluid and said hydraulic operation means changes the size of said chamber.

3. The device according to claim 2, wherein said hydraulic operation means comprises first and second wall portions of said reservoir, which are displaceable relative to each other to change the size of said chamber of said reservoir.

4. A device according to claim 3, wherein said hydraulic operation means comprise first and second wall portions of said reservoir, and said servo means provides relative displacement between said first and second wall portions of said reservoir to change the volume of said chamber of said reservoir.

5. A device according to claim 4, wherein said servo means comprises magnetic means, or electric means.

6. A device according to claim 3, wherein said servo means comprises hydraulic means.

7. A device according to claim 6, wherein said servo means comprises a servo reservoir defining a chamber containing servo fluid, and said hydraulic operation means comprise first and second wall portions of said servo reservoir, which are displaceable relative to each other to change the volume of said chamber of said servo reservoir.

8. A device according to claim 7, wherein said first and second wall portions of said servo reservoir are displaceable relative to each other by manual manipulation thereof, by magnetic means, by hydraulic means, or by electric control means.

9. A device according to claim 6, wherein said servo means comprises a servo reservoir and a fluid supply reservoir connected in a closed system and containing a further predetermined amount of fluid.

10. A device according to claim 9, wherein said fluid supply reservoir defines a chamber for said further predetermined amount of fluid and said hydraulic operation means are adapted to change the volume of said chamber and thereby control the amount of fluid in said servo reservoir.

11. A device according to claim 10, wherein said fluid supply reservoir comprises first and second wall portions, which are displaceable relative to each other to change the volume of said chamber of said fluid supply reservoir.

12. A device according to claim 11, wherein said fluid supply reservoir operates to servo reservoir with fluid from said fluid supply reservoir in response to a predetermined first displacement of said first wall portion of said fluid supply reservoir relative to said second wall portion of said fluid supply reservoir to increase the amount of fluid in said servo reservoir and operates said servo reservoir with fluid from said fluid supply reservoir in response to a predetermined second displacement of said first wall portion of said fluid supply reservoir relative to said second wall portion of said fluid supply reservoir to decrease the amount of fluid in said servo reservoir.

13. A device according to claim 2, further comprising a wireless remote control means for controlling said hydraulic operation means and for wireless transmission of energy from outside the patient's body to energy consuming implanted components of the food intake restriction device.

14. A device according to claim 13, wherein said wireless remote control means transmits signals, and further comprising an implanted energizer unit that draws energy from said signals.

15. A device according to claim 14, wherein said wireless remote control means transmits digital signals.

16. A device according to claim 14, wherein said wireless remote control means transmits said signals in the form of electromagnetic wave signals, and said energizer unit draws radiant energy from said electromagnetic wave signals as they are transmitted and transfers said radiant energy into electric energy.

17. A device according to claim 16, wherein said energizer unit comprises a coil for inducing an alternating current as electromagnetic wave signals are transmitted through said coil, and a rectifier for rectifying said alternating current.

18. A device according to claim 17, wherein said energizer unit comprises a capacitor adapted to tune said coil to a specific high frequency.

19. A device according to claim 13, further comprising a motor implanted in the patient for operating said hydraulic operation means.

20. A device according to claim 19, wherein said wireless remote control means transmits signals, and further comprising an implanted energizer unit that draws energy from said signals for the power of said motor.

21. A device according to claim 20, further comprising an implanted control unit for controlling said energizer unit to power said motor with energy in response to said signals transmitted by said wireless remote control means.

22. A device according to claim 20, wherein said wireless remote control means transmits said signals in the form of electromagnetic wave signals, said motor is an electric motor and said energizer unit draws radiant energy from said electromagnetic wave signals as they are transmitted and transfer said radiant energy into electric energy for powering said electric motor.

23. A device according to claim 22, wherein said energizer unit comprises a coil for inducing an alternating current as electromagnetic wave signals are transmitted through said coil, and a rectifier for rectifying said alternating current.

24. A device according to claim 23, wherein said energizer unit comprises a capacitor adapted to tune said coil to a specific high frequency.

25. A device according to claim 22, wherein said energizer unit comprises a rechargeable electric power supply for storing said electric energy and said control unit controls said rechargeable electric power supply to power said electric motor with energy in response to said signals.

26. A device according to claim 25, wherein said electric power supply comprises a capacitor.

27. A device according to claim 22, wherein said electric motor is a stepping motor.

28. A device according to claim 16, wherein said energizer unit comprises a battery, an electrically operable switch that connects said battery to said energy consuming implanted components in an "on" mode when said switch is powered and keeps said battery disconnected from said components in a "standby" mode when said switch is unpowered, and an electric power supply rechargeable with said electric energy for powering said switch.

29. A device according to claim 28, further comprising an electric motor implanted in the patient for operating said hydraulic operation means, wherein said switch connects said battery to said electric motor in said "on" mode when said switch is powered with electric energy from said electric power supply and keeps said battery disconnected from said electric motor in said "standby" mode when said switch is unpowered.

30. A device according to claim 29, further comprising an implanted control unit for controlling said energizer unit to power said electric motor with energy from said battery in response to said signals, when said switch is in its "on" mode.

31. A device according to claim 30, wherein said wireless remote control means transmits said signals in the form of electromagnetic wave signals, and said energizer unit draws radiant energy from said electromagnetic wave signals as they are transmitted and transfers said radiant energy into electric energy for charging said rechargeable electric power supply.

32. A device according to claim 31, wherein said energizer unit comprises a coil for introducing an alternating current as electromagnetic wave signals are transmitted through said coil, and a rectifier for rectifying said alternating current.

33. A device according to claim 32, wherein said energizer unit comprises a capacitor adapted to tune said coil to a specific high frequency.

34. A device according to claim 31, wherein said electric power supply comprises a capacitor.

35. A device according to claim 29, wherein said electric motor is a stepping motor.

36. A device according to claim 30, wherein said hydraulic operation means comprises a pump.

37. A device according to claim 36, wherein said. pump pumps in only one direction, and further comprising an adjustable valve that changes the direction of hydraulic fluid to either increase or decrease the amount of fluid in the reservoir.

38. A device according to claim 37, wherein said valve is manipulated either manually, mechanically, electrically, magnetically, or hydraulically.

39. A food intake restriction device for forming a stoma opening in the stomach or esophagus of a patient, comprising:

an elongated restriction member implanted in the patient forming an expandable and contractible cavity, said elongated restriction member formed into an at least substantially closed loop surrounding the patient's stomach or esophagus, and defining a restriction opening, the size of which is reduced upon expansion of said cavity and increased upon contraction of said cavity, a reservoir implanted in the patient defining a chamber for a predetermined amount of hydraulic fluid and connected to said cavity of said restriction member, and hydraulic operation means implanted in the patient for distributing fluid from said reservoir to said cavity to expand said cavity, and for distributing fluid from said cavity to said reservoir to contract said cavity, to thereby control the size of said restriction opening, wherein said reservoir defines a chamber for said predetermined amount of fluid and said hydraulic operation means changes the size of said chamber, and wherein said hydraulic operation means comprises first and second wall portions of said reservoir, which are displaceable relative to each other to change the volume of said chamber of said reservoir.

40. A device according to claim 39, wherein said first and second wall portions of said reservoir are displaceable relative to each other by manual manipulation thereof.

41. A device according to claim 40, wherein said first and second wall portions of said reservoir are displaceable relative to each other by manually pushing, pulling or rotating any of said wall portions in one direction.

42. A device according to claim 39, wherein said first and second wall portions of said reservoir are displaceable relative to each other by magnetic means, by hydraulic means, or by electric control means, such as an electric motor.

43. A device according to claim 39, wherein said hydraulic operation means distributes fluid from said reservoir to said cavity of said restriction member in response to a predetermined first displacement of said first wall portion of said reservoir relative to said second wail portion of said reservoir and distributes fluid from said cavity to said reservoir in response to a predetermined second displacement of said first wall portion relative to said second wall portion.

44. A device according to claim 39, further comprising a wireless remote control means for controlling said hydraulic operation device.

45. A device according to claim 44, wherein said wireless remote control means transmits digital signals for controlling said hydraulic operation device.

46. A device according to claim 44, wherein said wireless remote control means transmits energy wireless from outside the patient's body to energy consuming implanted components of the food intake restriction device.

47. A device according to claim 37, further comprising a motor implanted in the patient for operating said hydraulic operation means.

48. A food intake restriction device for forming a stoma opening in the stomach or esophagus of a patient, comprising:

an elongated restriction member implanted in the patient forming an expandable and contractible cavity, said elongated restriction member formed into an at least substantially closed loop surrounding the patient's stomach or esophagus, and defining a restriction opening, the size of which is reduced upon expansion of said cavity and increased upon contraction of said cavity, a reservoir implanted in the patient containing a predetermined amount of hydraulic fluid and connected to said cavity of said restriction member, and hydraulic operation means implanted in the patient for distributing fluid from said reservoir to said cavity to expand said cavity, and for distributing fluid from said cavity to said reservoir to contract said cavity, to thereby control the size of said restriction opening, said hydraulic operation means comprising an activatable pump for pumping fluid between said reservoir and said cavity of said restriction member, wherein said pump comprises a first activation member for activating said pump to pump fluid from said reservoir to said cavity of said restriction member and a second activation member for activating said pump to pump fluid from said cavity to said reservoir.

49. A device according to claim 48, wherein said first and second activation members are operable by manual manipulation thereof.

50. A device according to claim 49, wherein said first and second activation members are operable by manually pushing, pulling or rotating thereof in one direction.

51. A device according to claim 48, wherein at least one of said activation members operates when subjected to an external pressure exceeding a predetermined magnitude.

52. A device according to claim 48, wherein at least one of said first and second activating members are operable by magnetic means, or by hydraulic means, or by electric controls means such as an electric motor.

53. A device according to claim 48, further comprising a wireless remote control means for controlling said hydraulic operation device.

54. A device according to claim 53, wherein said wireless remote control means transmits digital signals for controlling said hydraulic operation device.

55. A device according to claim 53, wherein said wireless remote control means transmits energy wireless from outside the patient's body to energy consuming implanted components of the food intake restriction device.

56. A device according to claim 48, further comprising a motor implanted in the patient for operating said hydraulic operation means.

57. A food intake restriction device for forming a stoma opening in the stomach or esophagus of a patient, comprising:
- an elongated restriction member implanted in the patient forming an expandable and contractible cavity, said elongated restriction member formed into an at least substantially closed loop surrounding the patient's stomach or esophagus, and defining a restriction opening, the size of which is reduced upon expansion of said cavity and increased upon contraction of said cavity,
- a reservoir implanted in the patient containing a predetermined amount of hydraulic fluid and connected to said cavity of said restriction member, and
- hydraulic operation means implanted in the patient for distributing fluid from said reservoir to said cavity to expand said cavity, and for distributing fluid from said cavity to said reservoir to contract said cavity, to thereby control the size of said restriction opening,
- wherein said hydraulic operation means comprises a servo means.

58. A. device according to claim 57, wherein said hydraulic operation means comprises first and second wall portions of said reservoir, and said servo means provides relative displacement between said first and second wall portions of reservoir.

59. A device according to claim 57, wherein said servo means comprises magnetic means or electric means.

60. A device according to claim 57, wherein said servo means comprises hydraulic means.

61. A device according to claim 60, wherein said servo means comprises a servo reservoir defining a chamber containing servo fluid and said hydraulic operation means comprises first and second wall portions of said servo reservoir, which are displaceable relative to each other to change the volume of said chamber of said servo reservoir.

62. A device according to claim 61, wherein said first and second wall portions of said servo reservoir are displaceable relative to each other by manual manipulation thereof.

63. A device according to claim 62, wherein said first and second wall portions of said servo reservoir are displaceable relative to each other by manually pushing, pulling or rotating.

64. A device according to claim 61, wherein said first and second wall portions of said servo reservoir are displaceable relative to each other by magnetic means, by hydraulic means, or by electric control means such as an electric motor.

65. A food intake restriction device for forming a stoma opening in the stomach or esophagus of a patient, comprising:
- an elongated restriction member implanted in the patient forming an expandable and contractible cavity, said elongated restriction member formed into an at least substantially closed loop surrounding the patient's stomach or esophagus, and defining a restriction opening, the size of which is reduced upon expansion of said cavity and increased upon contraction of said cavity,
- a reservoir implanted in the patient containing a predetermined amount of hydraulic fluid connected to said cavity of said restriction member,
- hydraulic operation means implanted in the patient for distributing fluid from said reservoir to said cavity to expand said cavity, and for distributing fluid from said cavity to said reservoir to contract said cavity, to thereby control the size of said restriction opening, and
- a wireless remote control means for controlling said hydraulic operation means and for wireless transmission of energy from outside the patient's body to energy consuming implanted components of the food intake restriction device.

66. A device according to claim 65, wherein said wireless remote control means transmits signals, and further comprising an implanted energizer unit that draws energy from said signals.

67. A device according to claim 66, wherein said wireless remote control means transmits digital signals.

68. A device according to claim 66, wherein said wireless remote control means transmits and signals in the form of electromagnetic wave signals, and said energizer unit draws radiant energy from said electromagnetic wave signals as they are transmitted and transfers said radiant energy into electric energy.

69. A device according to claim 68, wherein said energizer unit comprises a coil for inducing an alternating current as electromagnetic wave signals are transmitted through said coil, and a rectifier for rectifying said alternating current.

70. A device according to claim 69, wherein said energizer unit comprises a capacitor adapted to tune said coil to a specific high frequency.

71. A device according to claim 65, further comprising a motor implanted in the patient for operating said hydraulic operation means.

72. A device according to claim 71, wherein said wireless remote control means transmits signals, and further comprising an implanted energizer unit that draws energy from said signals for the power of said motor.

73. A device according to claim 72, further comprising an implanted control unit for controlling said energizer unit to power said motor with energy in response to said signals transmitted by said wireless remote control means.

74. A device according to claim 72, wherein said wireless remote control means transmits said signals in the form of electromagnetic wave signals, said motor is an electric motor and said energizer unit draws radiant energy from said electromagnetic wave signals as they are transmitted and transfers said radiant energy into electric energy for powering said electric motor.

75. A device according to claim 74, wherein said energizer unit comprises a coil for inducing an alternating current as electromagnetic wave signals are transmitted through said coil, and a rectifier for rectifying said alternating current.

76. A device according to claim 75, wherein said energizer unit comprises a capacitor adapted to tune said coil to a specific high frequency.

77. A device according to claim 74, wherein said energizer unit comprises a rechargeable electric power supply for storing said electric energy and said control unit controls said rechargeable electric power supply to power said electric motor with energy in response to said signals.

78. A device according to claim 77, wherein said electric power supply comprises a capacitor.

79. A device according to claim 74, wherein said electric motor is a stepping motor.

80. A device according to claim 66, wherein said energizer unit comprises a battery, an electrically operable switch that connects said battery to said energy consuming implanted components in an "on" mode when said switch is powered and keeps said battery disconnected from said components in a "standby" mode when said switch it unpowered, and an electric power supply rechargeable with said electric energy for powering said switch.

81. A device according to claim 80, further comprising an electric motor implanted in the patient for operating said hydraulic operation means, wherein said switch connects said battery to said electric motor in said "on" mode when said switch is powered with electric energy from said electric power supply and keeps said battery disconnected from said electric motor in said "standby" mode when said switch is unpowered.

82. A device according to claim 81, further comprising an implanted control unit for controlling said energizer unit to power said electric motor with energy from said battery in response to said signals, when said switch is in its "on" mode.

83. A device according to claim 82, wherein said wireless remote control means transmits said signals in the form of electromagnetic wave signals, and said energizer unit draws radiant energy from said electromagnetic wave signals as they are transmitted and transfers said radiant energy into electric energy for charging said rechargeable electric power supply.

84. A device according to claim 83, wherein said energizer unit comprises a coil for inducing an alternating current as electromagnetic wave signals are transmitted. through said coil, and a rectifier for rectifying said alternating current.

85. A device according to claim 84, wherein said. energizer unit comprises a capacitor adapted to tune said coil to a specific high frequency.

86. A device according to claim 83, wherein said electric power supply comprises a capacitor.

87. A device according to claim 81, wherein said electric motor is a stepping motor.

88. A device according to claim 65, wherein said hydraulic operation means comprises a pump.

89. A device according to claim 88, wherein said pump pumps in only one direction, and further comprising an adjustable valve that changes the direction of hydraulic fluid to either increase or decrease the amount of fluid in the reservoir.

90. A device according to claim 89, wherein said valve is manipulated either manually, mechanically, electrically, magnetically, or hydraulically.

91. A food intake restriction device for forming a stoma opening in the stomach or esophagus of a patient, comprising:
an elongated restriction member implanted in the patient forming an expandable and contractible cavity, said elongated restriction member formed into an at least substantially closed loop surrounding the patient's stomach or esophagus, and defining a restriction opening, the size of which is reduced upon expansion of said cavity and increased upon contraction of said cavity,
a reservoir implanted in the patient containing a predetermined amount of hydraulic fluid and connected to said cavity of said restriction member,
hydraulic operation means implanted in the patient for distributing fluid from said reservoir to said cavity to expand said cavity, and for distributing fluid from said cavity to said reservoir to contract said cavity, to thereby control the size of restriction opening,
a battery implanted in the patient for powering implanted electric components of the food intake restriction device,
a switch implanted in the patient for switching the electric connection between said battery and said electric components, and
a wireless control means for wireless transmission of energy from outside the patient's body to energy consuming implanted components of the food intake restriction device including said switch.

92. A device according to claim 91, further comprising an electric motor implanted in the patient for operating said hydraulic operation means, wherein said battery powers said electric motor and said switch switches the electric connection between said battery and electric motor.

93. A device according to claim 91, wherein said wireless remote control means transmits signals, and further comprising an implanted energizer unit that draws energy from said signals.

94. A device according to claim 93, wherein said wireless remote control means transmits digital signals.

95. A device according to claim 93, wherein said wireless remote control means transmits and signals in the form of electromagnetic wave signals, and said energizer unit draws radiant energy from said electromagnetic wave signals as they are transmitted and transfers said radiant energy into electric energy.

96. A device according to claim 95, further comprising an implanted electric power supply rechargeable with said electric energy for powering said switch.

97. A device according to claim 96, wherein said electric power supply comprises a capacitor.

98. A device according to claim 91, wherein said wireless control means controls said hydraulic operation device.

99. A device according to claim 91, wherein said hydraulic operation means comprises a pump.

100. A device according to claim 99, wherein said pump pumps in only one direction, and further comprising an adjustable valve that changes the direction of hydraulic fluid to either increase or decrease the amount of fluid in the reservoir.

101. A device according to claim 100, wherein said valve is manipulated either manually, mechanically, electrically, magnetically, or hydraulically.

102. A. method of treating a patient with morbid obesity, comprising:
inflating the patient's abdomen with gas by penetration of the patient's skin;
introducing at least two laparoscopic trocars into the abdomen;
using the trocars to introduce into the abdomen one or more medical instruments and an elongated restriction member of a food intake restriction device having a cavity that can be expanded and contracted by the supply of hydraulic fluid thereto;
forming the restriction member into an at least substantially closed loop around the stomach or esophagus of the patient, the loop defining a restriction opening;
using the trocars to introduce into the abdomen a reservoir of the food intake restriction device for a predetermined amount of hydraulic fluid;
connecting the reservoir to the cavity of the restriction member,
using the trocars to introduce into the abdomen a hydraulic operation means of the food intake restriction device for distributing fluid between the reservoir and the cavity;
connecting the hydraulic operation means to the reservoir and cavity; and then when necessary for the patient's health or desired progress, in a non-invasive procedure, controlling the hydraulic operation means from a point outside the patient's body without physically penetrating the patient's body to change the size of the restriction opening.

103. A method according to claim 102, further comprising controlling the hydraulic operation means by a wireless remote control means.

104. A method according to claim 103, comprising using the wireless remote control means to transmit digital signals for controlling the hydraulic operation means.

105. A method according to claim 102, further comprising implanting in the patient an energizer unit capable of receiving wireless energy transmitted from outside the patient's body for powering implanted energy consuming components of the food intake restriction device including the hydraulic operation means.

106. A method of treating a patient with morbid obesity, comprising:
- implanting in the patient an elongated restriction member of a food intake restriction device having a cavity that can be expanded and contracted by the supply of hydraulic fluid thereto, so that the restriction member is formed into an at least substantially closed loop around the stomach or esophagus of the patient, the loop defining a restriction opening;
- implanting in the patient a reservoir of the food intake restriction device for a predetermined amount of hydraulic fluid and connecting the reservoir to the cavity of the restriction member;
- implanting in the patient a hydraulic operation means of the food intake restriction device for distributing fluid between the reservoir and the cavity;
- implanting in the patient an energizer unit capable of receiving wireless energy transmitted from outside the patient's body for powering implanted energy consuming components of the food intake restriction device including the hydraulic operation means; and
- when necessary for the patient's health or desired progress, in a non-invasive procedure, controlling the hydraulic operation means from a point outside the patient's body without physically penetrating the patient's body to change the size of the restriction opening.

107. A method according to claim 106, further comprising controlling the hydraulic operation means by a wireless remote control means.

108. A method according to claim 107, comprising using the wireless remote control means to transmit digital signals for controlling the hydraulic operation means.

109. A food intake restriction device for forming surgical application in the abdomen of a patient for forming a stoma opening in the stomach or esophagus of a patient, the device comprising:
- an elongated non-inflatable restriction member formed into at least substantially closed loop around the patient's stomach or esophagus, and defining a restriction opening,
- an adjustment device which mechanically adjusts said restriction member in said loop to change the size of restriction opening, said adjustment device comprising a servo means,
- a hydraulic operation means implanted in the patient for operating said adjustment device, and
- a reservoir implanted in the patient containing a first predetermined amount of fluid for supplying said hydraulic operation means with hydraulic fluid, wherein said servo means comprises a servo reservoir and a fluid supply reservoir connected in a closed system and containing a second predetermined amount of fluid.

110. A device according to claim 109, wherein said fluid supply reservoir defines a chamber for said second predetermined amount of fluid and said hydraulic operation means are adapted to change the volume of said chamber and thereby control the amount of fluid in said servo reservoir.

111. A device according to claim 110, wherein said fluid supply reservoir comprises first and second wall portions, which are displaceable relative to each other to change the volume of said chamber of said fluid supply reservoir.

112. A device according to claim 111, wherein said fluid supply reservoir operates said servo reservoir with fluid from said fluid supply reservoir in response to a predetermined first displacement of said first wall portion of said fluid supply reservoir relative to said second wall portion of said fluid supply reservoir to increase the amount of fluid in said servo reservoir and operates said servo reservoir with fluid from said fluid supply reservoir in response to a predetermined second displacement of said first wall portion of said fluid supply reservoir relative to said second wall portion of said fluid supply reservoir to decrease the amount of the fluid in said servo reservoir.

* * * * *